United States Patent
Piantoni et al.

(10) Patent No.: US 12,037,205 B2
(45) Date of Patent: Jul. 16, 2024

(54) METHOD AND APPARATUS FOR DEPOSITING DISCRETE ELEMENTS ON A SUPPORT ELEMENT

(71) Applicant: GDM S.p.A, Bologna (IT)

(72) Inventors: Matteo Piantoni, Albino (IT); Alessandro Zavalloni, Sesto ed Uniti (IT); Alessandro Saccomani, Cassano d'Adda (IT)

(73) Assignee: GDM S.p.A, Bologna (IT)

( * ) Notice: Subject to any disclaimer, the term of this patent is extended or adjusted under 35 U.S.C. 154(b) by 5 days.

(21) Appl. No.: 17/809,209

(22) Filed: Jun. 27, 2022

(65) Prior Publication Data

US 2022/0411204 A1    Dec. 29, 2022

(30) Foreign Application Priority Data

Jun. 28, 2021   (IT) .................... 102021000016817

(51) Int. Cl.
| | |
|---|---|
| *B65G 47/84* | (2006.01) |
| *A61F 13/15* | (2006.01) |
| *B65G 47/252* | (2006.01) |

(52) U.S. Cl.
CPC ...... *B65G 47/848* (2013.01); *A61F 13/15764* (2013.01); *B65G 47/252* (2013.01); *B65G 2201/022* (2013.01)

(58) Field of Classification Search
CPC ............... B65G 47/848; B65G 47/252; B65G 2201/022; A61F 13/15764;
(Continued)

(56) References Cited

U.S. PATENT DOCUMENTS

| | | | | |
|---|---|---|---|---|
| 6,648,122 B1 * | 11/2003 | Hirsch | ............ | A61F 13/15764 198/408 |
| 2004/0245069 A1 * | 12/2004 | Hook | ............ | B65G 47/848 198/377.04 |

(Continued)

FOREIGN PATENT DOCUMENTS

| | | | | |
|---|---|---|---|---|
| DE | 3635387 A | * | 4/1987 | ....... A61F 13/15601 |
| WO | 2015079367 A1 | | 6/2015 | |

(Continued)

OTHER PUBLICATIONS

Search Report issued in Italian Patent Application No. 202100016817; Issued Mar. 23, 2022; 10 pages.

*Primary Examiner* — Gene O Crawford
*Assistant Examiner* — Abby A Jorgensen
(74) *Attorney, Agent, or Firm* — Dilworth IP, LLC

(57) ABSTRACT

A method and apparatus for depositing discrete elements on a support element. The discrete elements may be separated from each other or joined to form a continuous web. The discrete elements are fed into a pick-up station defined at a rotor which includes circumferentially adjacent pick-up members. Each discrete element is associated with a respective pick-up member having a first orientation with respect to a respective second axis of rotation. Each pick-up member is moved along the rotation direction towards a release position downstream with an at least partially accelerated or decelerated motion. Each pick-up member is rotated about the respective second axis of rotation until it takes, at the release position, a second orientation. Each discrete element is released on a support element at the release position. Each pick-up member is subsequently moved towards the pick-up station with an at least partially decelerated or accelerated motion.

10 Claims, 4 Drawing Sheets

(58) Field of Classification Search
CPC ........... B65H 2301/33214; B65H 2301/33222; B65H 2301/4472; B65H 2301/44735; B65H 2406/2454; B65H 2801/57; B65H 29/241; B65H 2220/02; B65H 2220/01
See application file for complete search history.

(56) References Cited

U.S. PATENT DOCUMENTS

| | | | | |
|---|---|---|---|---|
| 2013/0296149 A1* | 11/2013 | Schneider | ......... | A61F 13/15707 493/8 |
| 2016/0106596 A1* | 4/2016 | Tameishi | ............. | B65G 47/244 198/802 |
| 2018/0104112 A1* | 4/2018 | Piantoni | ............ | A61F 13/15804 |
| 2018/0362266 A1* | 12/2018 | Schneider, I | ......... | B65G 47/848 |
| 2019/0240077 A1* | 8/2019 | Ogawa | .............. | A61F 13/15764 |

FOREIGN PATENT DOCUMENTS

| | | | | |
|---|---|---|---|---|
| WO | WO-2015079367 A1 * | 6/2015 | ....... | A61F 13/15756 |
| WO | 2016162850 A1 | 10/2016 | | |
| WO | WO-2016162850 A1 * | 10/2016 | ....... | A61F 13/15764 |
| WO | 2018037304 A1 | 3/2018 | | |
| WO | WO-2018037304 A1 * | 3/2018 | ....... | A61F 13/15764 |
| WO | WO-2019058256 A1 * | 3/2019 | ....... | A61F 13/15723 |

\* cited by examiner

METHOD AND APPARATUS FOR DEPOSITING DISCRETE ELEMENTS ON A SUPPORT ELEMENT

FIELD OF THE INVENTION

The present invention relates to a method for depositing discrete elements on a support element.

BACKGROUND OF THE INVENTION

The invention also relates to an apparatus for depositing discrete elements on a support element. Such apparatus preferably performs the method of the invention.

Throughout this description and in the subsequent claims, the term "discrete element" is used to indicate an element having a predetermined shape that is structurally (and preferably also visually) distinguishable from adjacent similar elements either because it is physically separated from adjacent similar elements or because it is physically joined to adjacent similar elements at lines of mutual connection that define lines of structural discontinuity between two adjacent similar elements.

In this description reference is made to the exemplary and non-limiting case in which the discrete element is a base or accessory component for the manufacture of a hygienic article.

Hygienic articles of the absorbent type, in particular baby nappies, sanitary towels or adult incontinence products, are known. They comprise a plurality of components, including a non-woven layer, an impermeable layer and an absorbent padding layer enclosed between the non-woven layer and the impermeable layer. Such layers are typically obtained starting from respective continuous webs.

Typically, a packaging machine of the known type for the manufacture of hygienic absorbent articles of the type described above comprises an advancement line of a continuous web of impermeable material along which a plurality of operating units are arranged, these units being configured to feed the additional components necessary to complete the hygienic absorbent article to the continuous web.

Each operating unit comprises an apparatus configured to receive one after the other a component and to perform a specific processing on the component itself (e.g., a cutting operation of the component into discrete elements) and an apparatus configured to deposit the component thus processed (e.g., the aforementioned discrete elements) on another component (e.g., the aforementioned continuous web of impermeable material).

The Applicant has observed that, in order to increase the productivity and flexibility of the packaging machines for packaging sanitary absorbent articles, suitable arrangements should be made to ensure that the discrete elements can be deposited on the continuous web of impermeable material with different deposition pitches and orientations depending on various specific features, such as for example the type and/or shape of the sanitary absorbent article to be packaged.

The problem at the basis of the present invention is to meet the above-mentioned requirement.

SUMMARY OF THE INVENTION

The present invention therefore relates, in a first aspect thereof, to a method for depositing discrete elements on a support element.

These discrete elements may be separated from each other or joined to each other to form a continuous web having a perforation line between each pair of adjacent discrete elements.

Preferably, said discrete elements are fed one after the other into a pick-up station defined at an apparatus comprising a rotor rotatable about a first axis of rotation along a rotation direction.

Preferably, said rotor comprises a plurality of circumferentially adjacent pick-up members.

Preferably, said support element is fed at a release position defined downstream of the pick-up station with reference to said rotation direction.

Preferably, each discrete element is stably associated with a respective pick-up member having in said pick-up station a first orientation with respect to a respective second axis of rotation orthogonal to the first axis of rotation.

Preferably, each pick-up member is moved along said rotation direction from the pick-up station towards the release position with an at least partially accelerated or decelerated motion.

Preferably, during the movement of each pick-up member along said rotation direction, said pick-up member rotates about the respective second axis of rotation until it takes, at the release position, a second orientation different from said first orientation.

Preferably, each discrete element is released from the respective pick-up member on said support element at said release position.

Preferably, each pick-up member is moved along said rotation direction from the release position towards the pick-up station with an at least partially decelerated or accelerated motion.

In a second aspect thereof, the present invention relates to an apparatus for depositing discrete elements on a support element.

Preferably, a stator is provided.

Preferably, a rotor is provided, the rotor being rotatable about a first axis of rotation along a rotation direction.

Preferably, the rotor comprises a plurality of circumferentially adjacent pick-up members.

Preferably, said pick-up members are movable along said rotation direction.

Preferably, each of said pick-up members is rotatable about a respective second axis of rotation orthogonal to the first axis of rotation.

Preferably, first control members are provided, the first control members being configured to control the movement of the pick-up members along said rotation direction.

Preferably, said first control members are configured to move the pick-up members between a pick-up station and a release position defined downstream of the pick-up station along said rotation direction.

Preferably, at the pick-up station the pick-up members have a first relative distance from each other.

Preferably, at the release position the pick-up members have a second relative distance from each other, said second relative distance being different from the first relative distance.

Preferably, second control members are provided, the second control members being configured to control the orientation of each pick-up member.

Preferably, said second control members are configured to arrange each pick-up member with a first orientation with respect to the respective second axis of rotation when the pick-up members are at the pick-up station.

Preferably, said second control members are configured to arrange each pick-up member with a second orientation with respect to a respective second axis of rotation when the pick-up members are at the release position.

In the present description and in the subsequent claims, the expression "downstream" is used to indicate an angular position defined beyond another angular position with reference to a predetermined rotation direction.

In this description and in the subsequent claims, the terms "radially" and "radial" are used to indicate any direction perpendicular to an axis of rotation of the rotor of the apparatus. "Radially outer" is used to indicate a position defined along a radial direction and which is further away from the aforesaid axis of rotation than that of a reference element, whereas "radially inner" is used to indicate a position defined along a radial direction and which is closer to the aforesaid axis of rotation than that of a reference element.

The term "circumferentially" is used to indicate a direction defined about the aforesaid axis of rotation.

The terms "axially" and "axial" are instead used to indicate a direction coinciding with or parallel to the aforesaid axis of rotation. "Axially inner" is used to indicate a position defined along an axial direction and which is closer to a transverse plane of symmetry of the rotor than that of a reference element, whereas "axially outer" is used to indicate a position defined along an axial direction and which is further away from the transverse plane of symmetry of the rotor than that of a reference element. When the expressions "axially inner" and "axially outer" are used with reference to a pair of reference elements, they are intended to indicate, respectively, a position interposed to said pair of reference elements, i.e. defined between said pair of reference elements, and a position not interposed between said pair of reference elements.

In accordance with the present invention, the provision of pick-up members that decelerate or accelerate when they are moved towards the pick-up station and accelerate or decelerate when they are moved towards the release position, together with the possibility of providing such pick-up members with an orientation at the release position that is different from the one that they have at the pick-up station, makes it possible to achieve the desired increase in productivity and flexibility of the packaging machines for packaging absorbent hygienic articles.

In any one or both of the aspects discussed above, the present invention may have at least one of the preferred features described below. These features may therefore be present individually or in combination with each other, unless expressly stated otherwise.

In a first preferred embodiment of the invention, discrete elements are separated from each other when they are fed to the apparatus said. This embodiment is particularly preferred in the case of discrete elements that lack elasticity and which therefore do not risk to be subjected to a shrinkage during transfer towards the pick-up station of the apparatus after they have been cut from a continuous web and separated from each other.

In a second preferred embodiment of the invention, said discrete elements are joined to each other when they are fed to the apparatus to form a continuous web having a perforation line between each pair of adjacent discrete elements. In this embodiment, the discrete elements may be separated along the perforation lines during the movement of the pick-up members from the pick-up station towards the release position, when the pick-up members move away from each other during this movement. This embodiment is particularly preferred in the case of discrete elements that have a certain degree of elasticity and which would therefore risk to be subjected to a shrinkage during transfer towards the pick-up station of the apparatus if they were cut beforehand.

Preferably, each discrete element is released by the respective pick-up member directly onto the support element.

The support element can be fed close to the pick-up members by a roller or a conveyor belt, which in addition to allow the desired stability of the support element to be maintained, also act as a contrast while discrete elements are being applied on the support element.

Preferably, the movement of each pick-up member along said rotation direction is obtained as a consequence of an oscillation of a respective lever with respect to a respective axis parallel to the first axis of rotation.

Preferably, said lever is integral in rotation with a support slide of the pick-up member, said support slide sliding on a pair of annular guides.

Each of said annular guides can be made as a single piece or be defined by a plurality of angular sectors circumferentially adjacent to each other.

Preferably, said lever is kinematically connected to a first cam follower coupled with an eccentric cam which is eccentric with respect to the first axis of rotation.

Preferably, said oscillation is obtained by a movement of the first cam follower in the eccentric cam.

Preferably, said lever is arranged in a radially inner position with respect to said pair of annular guides.

More preferably, said lever is integrally connected to a portion of the support slide arranged in an axially inner position with respect to said pair of annular guides. In this way, the support slide is stressed by the respective lever at an intermediate axial position of the support slide, which can then move on the pair of annular guides with a high degree of smoothness and stability, avoiding unbalanced wear on the two annular guides. This expedient also makes it possible to limit the dimensions of the support slides without running the risk that they may deform due to the stress imparted by the respective lever.

In an alternative embodiment, said lever is arranged in an axially outer position with respect to said pair of annular guides and is integrally connected to a portion of the support slide arranged in an axially outer position with respect to said pair of annular guides.

Preferably, the movement of each pick-up member about the respective second axis of rotation is obtained as a consequence of a movement of a second cam follower in a cylindrical or spheroconic cam.

Preferably, said second cam follower is kinematically coupled to the pick-up member.

Preferably, said cylindrical or spheroconic cam is arranged in an axially outer position with respect to said pair of annular guides. This positioning allows easy access to the aforementioned cam during maintenance operations and enables the application of a covering element on this cam that is configured to prevent lubricating grease present therein from escaping from the cam and fouling the components adjacent to it.

In an alternative embodiment, said cylindrical or spheroconic cam is arranged in an axially inner position with respect said the pair of annular guides.

Preferably, stably associating each discrete element with the respective pick-up member comprises exerting a suction action on said discrete element through a suction duct associated with said pick-up member.

Preferably, said suction conduit extends at least partially in a radially inner position with respect to said pick-up member. This makes it possible to limit the axial dimension of the apparatus implementing the method of the invention. Arranging the cylindrical or spheroconic cam in an axially outer position with respect to the pair of annular guides leaves, in a radially inner position with respect to the pick-up member, the space that is necessary for housing the suction duct.

Preferably, each pick-up member is associated with a support slide sliding on a pair of annular guides.

Preferably, said first control members comprise an eccentric cam which is eccentric with respect to the first axis of rotation.

Preferably, said first control members comprise a plurality of first cam followers coupled to said eccentric cam.

Preferably, said first control members comprise a plurality of levers.

Preferably, each of said levers is integral in rotation with a respective support slide of a pick-up member.

Preferably, each of said levers is kinematically connected to a respective first cam follower.

Preferably, each of said levers is arranged in an axially inner or axially outer position with respect to said pair of annular guides.

Preferably, each of said levers is solidly connected to a portion of the respective support slide arranged in an axially inner or axially outer position with respect to said pair of annular guides.

Preferably, said eccentric cam is formed on an axially inner surface of a front body of the stator. This positioning allows easy access to the aforesaid cam during maintenance operations and/or when, for example during a format change, it is necessary to replace the eccentric cam with another one designed to allow a different feed pitch of the discrete elements in the pick-up station and/or a different deposition pitch of the discrete elements on the support element.

Preferably, said second control members comprise a cylindrical or spheroconic cam.

Preferably, said second control members comprise a plurality of second cam followers coupled to said cylindrical or spheroconic cam.

Preferably, each of said second cam followers is kinematically coupled to a respective pick-up member.

Preferably, said cylindrical or spheroconic cam is arranged in an axially outer or axially inner position with respect to said pair of annular guides.

Preferably, each of said second cam followers is supported in a cantilevered manner by the respective support slide.

Preferably, each of said second cam followers is kinematically coupled to the respective pick-up member through an oscillating glyph mechanism. This mechanism is small in size and can therefore be housed inside small-sized support slides.

Preferably, said cylindrical or spheroconic cam is formed on a radially outer surface of a rear body of the stator.

Preferably, a first plurality of support slides comprises a pair of wheels coupled to a radially outer surface of a first annular guide of the pair of annular guides.

Preferably, a first plurality of support slides comprises a single wheel coupled to a radially outer surface of the other annular guide.

Preferably, a second plurality of support slides comprises a single wheel coupled to the radially outer surface of said first annular guide.

Preferably, a second plurality of support slides comprises a pair of wheels coupled to the radially outer surface of the other annular guide.

Preferably, each support slide of said first plurality of support slides is arranged between two respective support slides of said second plurality of support slides.

In this way, an alternation in a circumferential direction of support slides having a pair of wheels and of support slides having a single wheel is provided on each annular guide. This allows the support slides to be brought closer to each other in the pick-up station, thus allowing discrete elements of even small dimensions to be deposited on the relative pick-up members, with obvious advantages in terms of productivity and operational flexibility.

Preferably, each pick-up member is in fluid communication with a respective suction conduit.

Preferably, said suction conduit extends at least partially in a radially inner position with respect to said pick-up member.

BRIEF DESCRIPTION OF THE DRAWINGS

Further characteristics and advantages of the present invention will become clearer from the following detailed description of preferred implementations/embodiments thereof, made with reference to the attached drawings and provided by way of indicative and non-limiting example. In such drawings.

DETAILED DESCRIPTION

Figure 1:
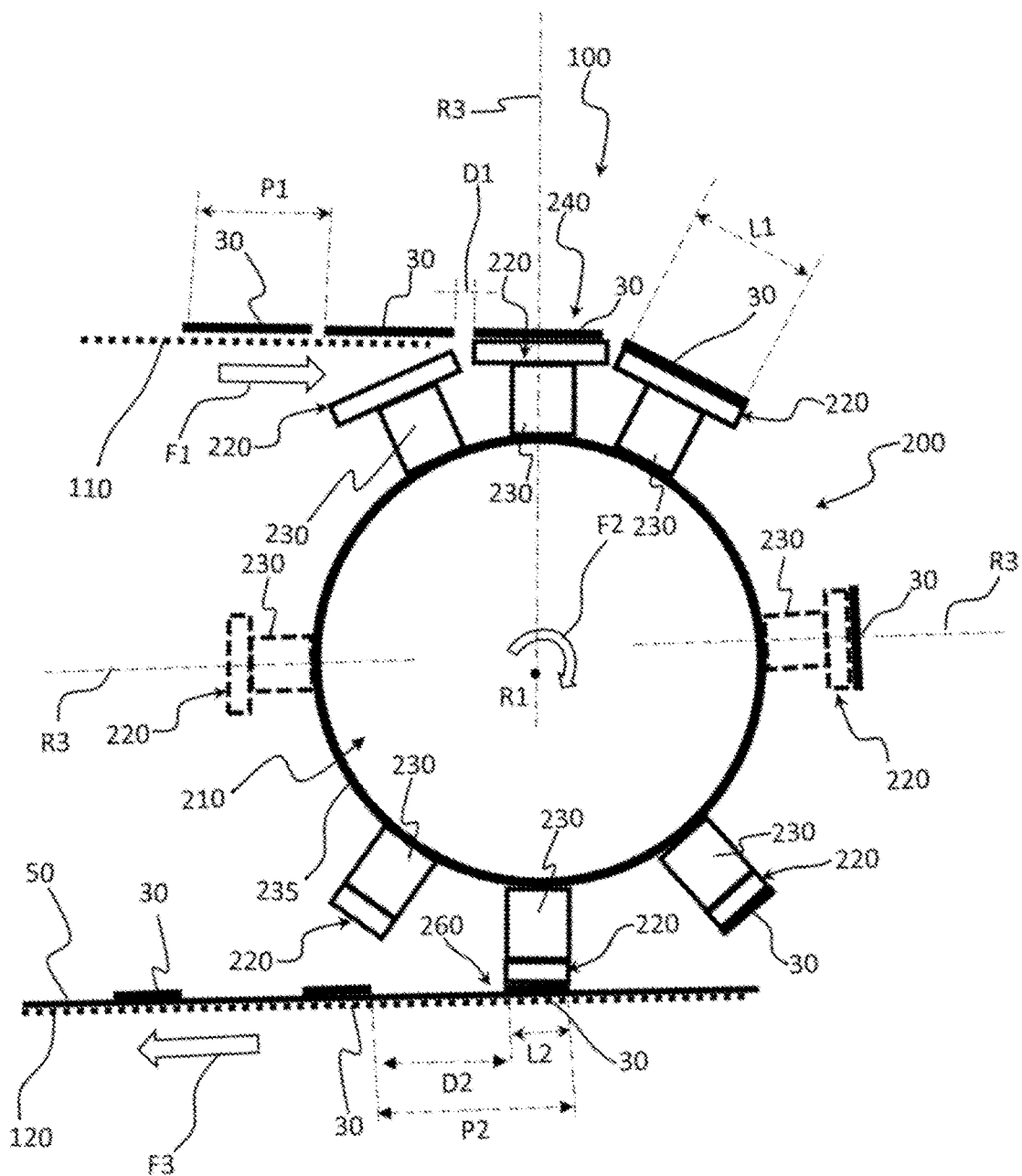
FIG. 1 is a representative schematic view of a machine in which the method of the present invention is carried out.

With reference to FIG. 1, a packaging machine for the manufacture of components of hygienic articles is labelled with 100.

The packaging machine 100 is part of a plant for packaging hygienic articles and carries out a part of the packaging operation for packaging these hygienic articles.

The packaging machine 100 comprises a conveyor belt 110 configured to feed one after the other a plurality of discrete elements 30 into a pick-up station 240 defined at an apparatus 200 in accordance with the present invention.

In the non-limiting example shown in FIG. 1, the discrete elements 30 are separated from each other. In particular, they have been suitably created, for example by repeated cutting of a continuous web, before being deposited on the conveyor belt 110 or after having been deposited on the conveyor belt and before being transferred to the apparatus 200.

However, the case in which the discrete elements 30 are fed to the apparatus 200 joined to each other to form a continuous web having a perforation line between each pair of adjacent discrete elements 30 is also foreseen.

The conveyor belt 110 advances along a feed direction F1 substantially tangential to an ideal circumference that circumscribes the apparatus 200 and transfers the discrete elements 30 to the apparatus 200 at a predetermined feed pitch P1.

The conveyor belt 110 comprises suction members configured to retain the discrete elements 30 while they move along the feed direction F1.

A support element 50, which is, for example, a continuous web of impermeable material, is fed at a release position 260 arranged downstream of the pick-up station 240 with reference to a rotation direction F2 of the apparatus 200 about an axis of rotation R1 thereof. In the example shown in FIG. 1, the rotation direction F2 is a clockwise direction and the release position 260 is placed at approximately 180° with respect to the pick-up station 240 with reference to the rotation direction F2.

The apparatus 200 deposits one after the other the discrete elements 30 on the support element 50.

The support member 50 is arranged on a conveyor belt 120 that advances along a substantially rectilinear advancement direction F3. The advancement direction F3 is substantially tangent to the ideal circumference circumscribing the apparatus 200. In the non-limiting example shown in FIG. 1, the advancement direction F3 is opposed to the feed direction F1.

Once deposited on the support element 50, the latter and the discrete elements 30 deposited thereon are moved through the conveyor belt 120 along the advancement direction F3 away from the packaging machine 100, for example to move onto other machines configured to complete the packaging of the hygienic articles.

The conveyor belt 120 comprises suction members configured to retain the support element 50 and the discrete elements 30 while they move along the advancement direction F3.

The apparatus 200 is configured to properly handle the discrete elements 30 after having picked them up from the conveyor belt 110 at the pick-up station 240 and to deposit them on the support element 50.

In particular, the discrete elements 30 have, in the pick-up station 240, an orientation different from the one that they have on the support element 50.

Assuming that each discrete element 30 has a longitudinal dimension L1 and a transverse dimension L2 that is less than the longitudinal dimension L1, in the pick-up station 240 the discrete elements 30 are oriented such that the longitudinal direction L1 is substantially tangent to the aforementioned ideal circumference of the apparatus 200, whereas on the support element 50 the discrete elements 30 are oriented such that the transverse direction L2 is substantially tangent to the aforementioned ideal circumference of the apparatus 200.

Furthermore, the discrete elements 30 have, in the pick-up station 240, a mutual distance D1 correlated to the feed pitch P1, and thus to the pitch with which they are arranged on the conveyor belt 110, whereas on the support element 50 they have a mutual distance D2 different from D1 and correlated to a deposition pitch P2 of the discrete elements 30 on the support element 50.

In the example shown in the accompanying figures, P2 is greater than P1 and thus D2 is greater than D1.

Thus, in the example shown in FIG. 1, the apparatus 200 is configured to cause, during movement from the pick-up station 240 to the release position 260, each discrete element 30 to rotate by about 90° with respect to a respective axis of rotation R3 orthogonal to the axis of rotation R1 in order to take on the support element 50 the desired orientation and to move away from the successive discrete element 30 with reference to the rotation direction F2 in order to obtain on the support element 50 the desired deposition step P2.

In the case where the discrete elements 30 are joined to each other to form a continuous web, the movement of each discrete element 30 away from the following one during their movement along the rotation direction F2 results in the separation by tearing of the discrete elements 30 at their respective perforation lines.

Figure 2:
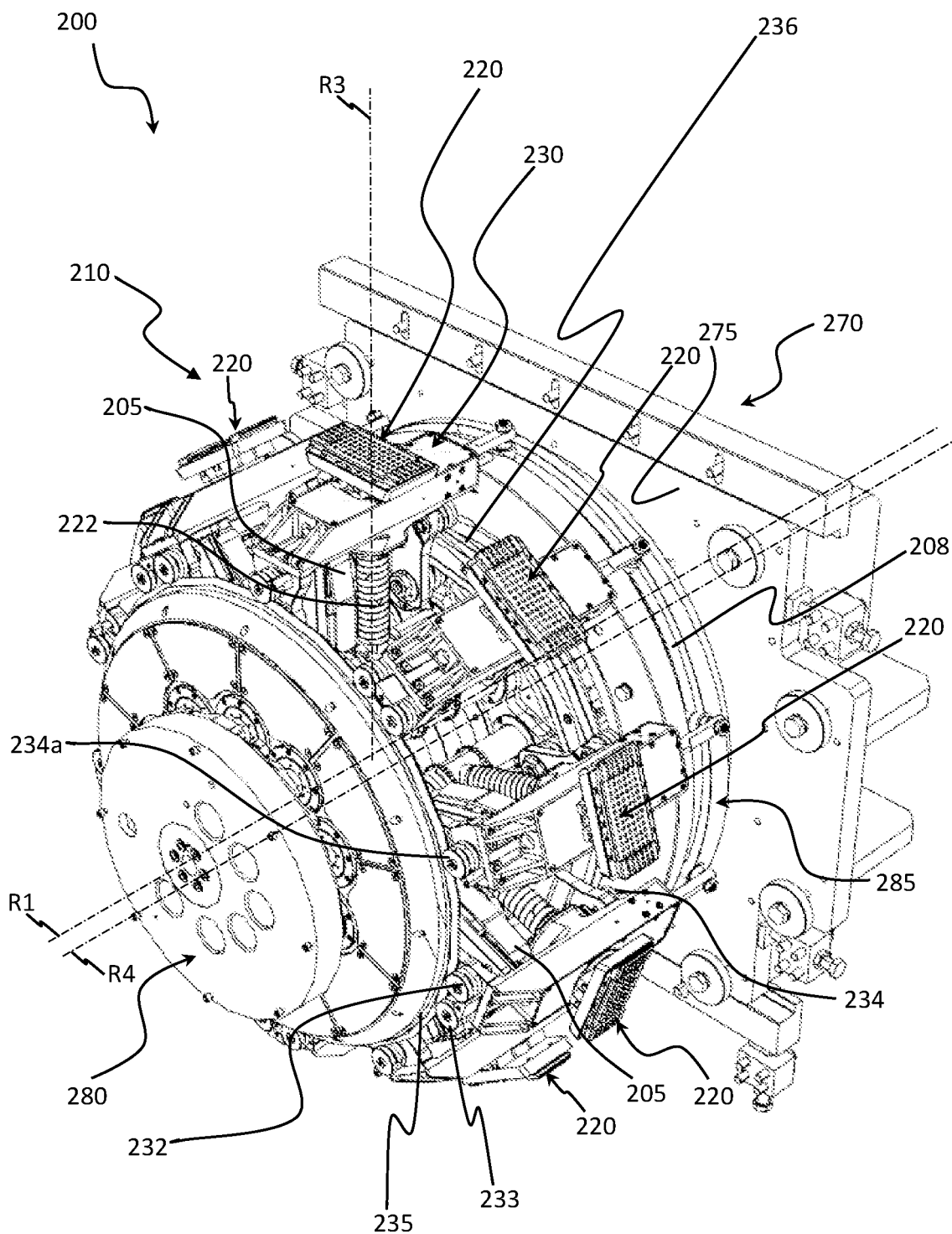
FIG. 2 is a front perspective schematic view of an apparatus of the machine of FIG. 1, in an exemplary and non-operational configuration thereof.

The apparatus 200 comprises a stator 270 and a rotor 210 that is rotatable about the axis of rotation R1 along the direction F2 (FIG. 2).

The stator 270 comprises a base 275, a front body 280, and a rear body 285.

Throughout this description and in the subsequent claims, the terms "front" and "rear" are used to indicate a relative axial position with respect to the base 275, respectively further away from the base 275 and closer to the base 275.

The base 275 is substantially orthogonal to the axis of rotation R1. The rear body 285 is axially interposed between the rotor 210 and the base 275. The rotor 210 is axially interposed between the front body 280 and the rear body 285.

The rotor 210 comprises a plurality of circumferentially adjacent pick-up members 220 each of them being configured to support, in the path between the pick-up station 240 and the release position 260, a respective discrete member 30.

Each pick-up member 220 is movable in rotation about the respective axis of rotation R3 orthogonal to the axis of rotation R1. As a result of this rotation, the discrete elements 30 change orientation.

Each pick-up member 220 has surface openings 221 to allow the respective discrete element 30 to be retained by suction during movement of the discrete elements 30 from the pick-up station 240 to the release position 260.

For this purpose, each pick-up member 220 is in fluid communication with a respective suction conduit 222.

Figure 3:
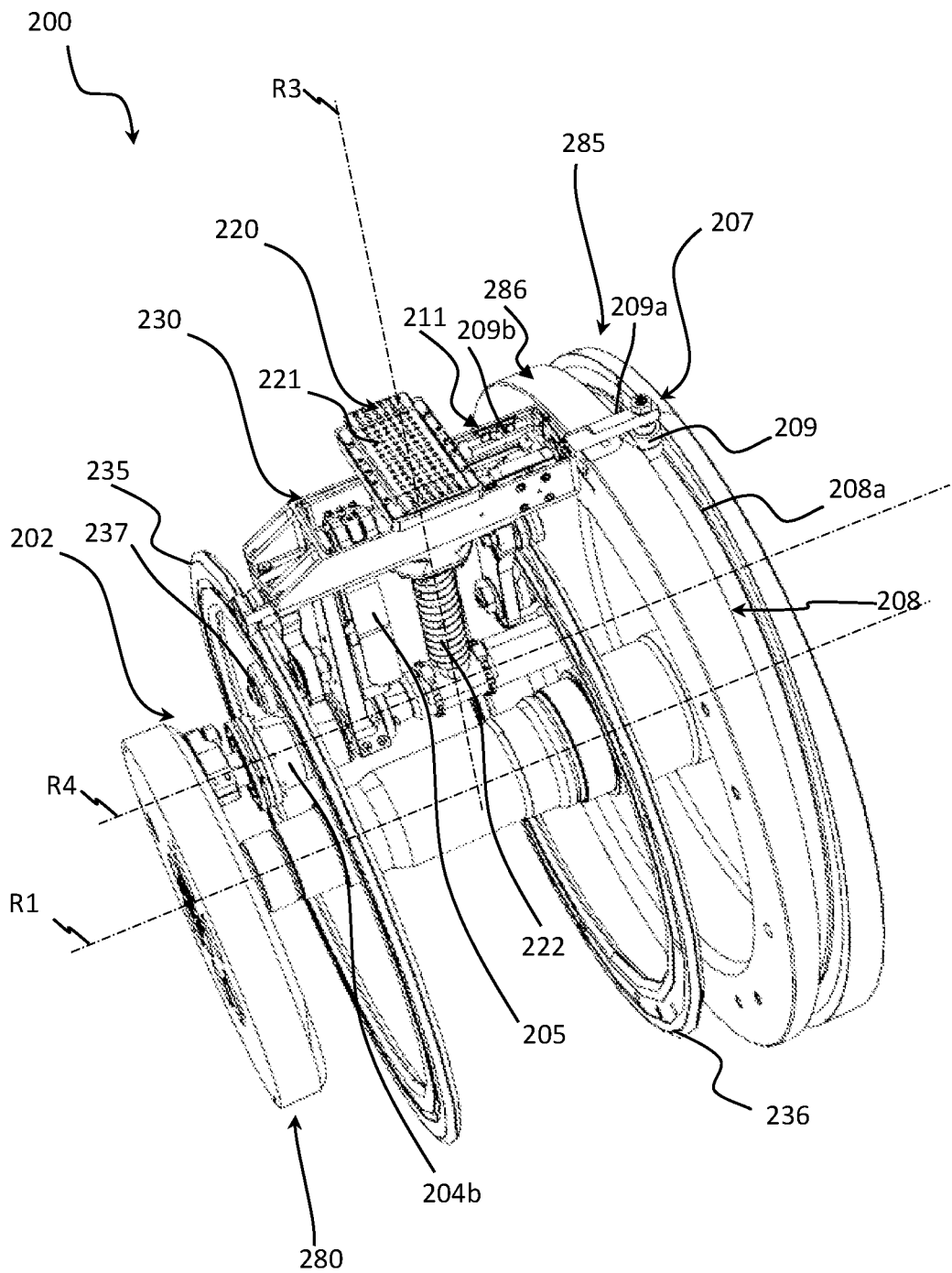
FIG. 3 is a schematic perspective side view of a portion of the apparatus of FIG. 2, in which only some of its components are shown.
Figure 4:
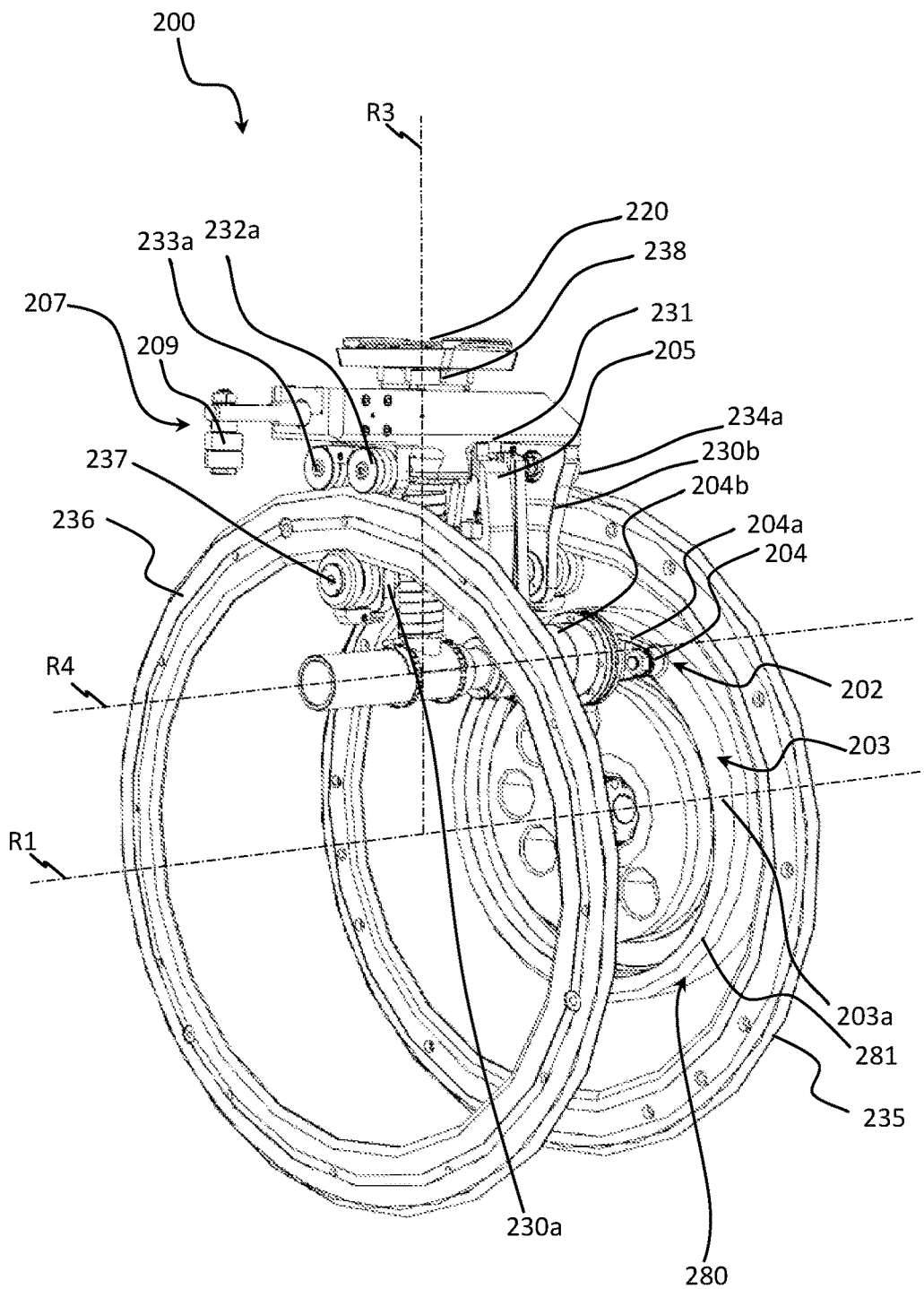
FIG. 4 is a schematic perspective rear view of the apparatus of FIG. 2, in which only some of its components are shown.

In the non-limiting example shown in FIGS. 2-4, the suction conduit 222 extends radially in a radially inner position with respect to the pick-up member 220.

Each pick-up member 220 is rotatably associated with a support slide 230 which is slidably associated, at the two opposed end portions thereof, with a pair of annular guides 235, 236 that are parallel and concentric with respect to the axis of rotation R1 (FIGS. 2-4). The support slides 230, and thus the pick-up members 220, are therefore axially interposed between the annular guides 235, 236.

In the example shown herein, each of the annular guides 235, 236 is made as a single piece.

The annular guides 235, 236 are fixed to the rotor 210 and rotate with respect to the stator 270 integrally with the rotor 210.

Each support slide 230 (and thus each pick-up member 220) is moved along the rotation direction F2 from the pick-up station 240 towards the release position 260 with an at least partially accelerated motion. In this way, after passing through the pick-up station 240, each pick-up member 220 moves away from the following pick-up member 220 along the rotation direction F2, obtaining the desired deposition pitch P2 in the release position 260.

During the movement of each support slide 230 along the rotation direction F2 from the pick-up station 240 to the release position 260, each pick-up member 220 is controlled to rotate about the respective axis of rotation R3 until it takes the desired orientation at the release position 260. In the non-limiting example shown in FIG. 1, a pick-up member 220 is represented by dotted lines, about halfway between the pick-up station 240 and the release position 260, while it is rotating about the axis of rotation R3.

After each discrete element 30 has been released from the respective pick-up member 220 on the support element 50, each support slide 230 is moved along the rotation direction F2 from the release position 260 towards the pick-up station 240 with an at least partially decelerated motion. In this way, after passing through the release position 260, each pick-up member 220 moves closer to the preceding pick-up member 220 along the rotation direction F2, obtaining in the pick-up station 240 a mutual distancing of the pick-up members 220 that is consistent with the feed pitch P1.

During the movement of each support slide 230 along the rotation direction F2 from the release position 260 to the pick-up station 240, each pick-up member 220 is controlled to rotate about the respective rotation axis R3 until it takes the desired orientation in the pick-up station 240. In the non-limiting example shown in FIG. 1, a pick-up member 220 is represented in dotted lines, about halfway between the release position 260 and the pick-up station 240, while it is rotating about the axis of rotation R3.

FIG. 2 shows a plurality of support slides 230 placed circumferentially equidistant from each other, with the respective pick-up members 220 having all the same orientation. This FIG. 2 is useful for illustrative purposes but it does not correspond to a real operating configuration of the apparatus 200 during the implementation of the method of the invention, such real operating configuration being instead shown in FIG. 1 and providing that the support slides 230 are not all equally spaced from each other along the rotation direction F2 and the pick-up members 220 do not have all the same orientation along the rotation direction F2.

The movement of each support slide 230 along the rotation direction F2 is controlled by a respective control member 202, whereas the rotation of each pick-up member 220 about the respective axis of rotation R3 is controlled by a respective control member 207. These control members are shown in FIGS. 3 and 4.

The control members 202 comprise an eccentric cam 203 kinematically connected to each support slide 230 through respective first kinematic linkage members.

The eccentric cam 203 has an axis of symmetry R4 which is parallel to the axis of rotation R1, and eccentric with respect to the latter, and it is defined by a groove 203a formed on an axially inner surface 281 of the front body 280 (FIG. 4).

The first kinematic linkage members comprise a cam follower 204 coupled to the eccentric cam 203 and a lever 205 coupled to the cam follower 204 and to the respective support slide 230.

The support slide 230 is integral in rotation with the lever 205 and it is moved.

The lever 205 is arranged in an axially inner position with respect to the pair of annular guides 235, 236 and is integrally connected to a portion 231 of the support slide 230, said portion 231 being arranged in an axially inner position with respect to the pair of annular guides 235, 236.

The movement of each support slide 230, and therefore of each pick-up member 220, along the rotation direction F2 from the pick-up station 240 to the release position 260 and subsequently from the release position 260 to the pick-up station 240 is obtained as a consequence of a rotation of the rotor 210 with respect to the rotation axis R1 and of an oscillation of the respective lever 205 with respect to a respective axis R4 parallel to the first rotation axis R1 (FIGS. 3 and 4). This oscillation is obtained by a displacement of the cam follower 204 in the eccentric cam 203.

The first kinematic linkage members further comprise a lever 204a fixed to the cam follower 204 and pivoted on a rotation pin 204b which is rotatable about the axis R4 and integral in rotation with the lever 205.

In the non-limiting example shown in FIGS. 3 and 4, the suction duct 222 extends in a radial direction substantially parallel to the lever 205.

As shown in FIG. 3, the control members 207 comprise a spheroconic cam 208 kinematically connected to each pick-up member 220 through respective second kinematic linkage members.

The second kinematic linkage members comprise a cam follower 209 coupled to the spheroconic cam 208 and to a respective pick-up member 220. The movement of each pick-up member 220 about the respective axis of rotation R3 is obtained by a movement of the cam follower 209 in the spheroconic cam 208.

The spheroconic cam 208 has an axis of symmetry coincident with the axis of rotation R1 and is defined by a groove 208a formed on a radially outer surface 286 of the rear body 285.

The spheroconic cam 208 is arranged in an axially outer position with respect to the pair of annular guides 235, 236.

In the non-limiting example shown in FIG. 3, the cam follower 209 is kinematically coupled to the pick-up member 220 through an oscillating glyph mechanism 211. This mechanism comprises a first arm 209a fixed to the cam follower 209 and a second arm 209b connected to the pick-up member 220 and properly connected to the first arm 209a.

Each support slide 230 is slidingly associated with the annular guides 235, 236 through a plurality of wheels.

Specifically, a first plurality of support slides 230 comprises a pair of wheels 232, 233 coupled to a radially outer surface of the annular guide 235 and a single wheel 234 coupled to a radially outer surface of the annular guide 236 (FIG. 2), whereas a second plurality of support slides 230 comprises a single wheel 234a coupled to the radially outer surface of the annular guide 235 and a pair of wheels 232a, 233a coupled to the radially outer surface of the annular guide 236 (FIG. 4).

As shown in FIG. 2, each support slide 230 of the first plurality of support slides 230 is arranged between two respective support slides 230 of the second plurality of support slides 230.

In a front view of the rotor 210, the single wheel 234, 234a of each support slide 230 is circumferentially interposed between the pair of wheels 232, 233 and the pair of wheels 232a, 233a.

Preferably, the radially outer surfaces of the annular guides 235, 236 have a wedge-shaped cross-section. Correspondingly, the wheels 232, 233, 232a, 233a, 234, 234a of the support slides 230 preferably have respective circumferential grooves also having a wedge-shaped cross-section.

Each support slide 230 is coupled to the annular guides 235, 236 also at the radially inner surfaces of the annular guides 235, 236 through a respective wheel 237 (FIGS. 3 and 4).

The wheels 237 are radially opposed to the pairs of wheels 232, 233 and 232a, 233a, and to the single wheels 234 and 234a. In this way, the support slides 230 are radially constrained to the annular guides 235, 236.

Preferably, the radially inner surfaces of the annular guides 235, 236 have a wedge-shaped cross-section. Correspondingly, the wheels 237 of the support slides 230 preferably have respective circumferential grooves also having a wedge-shaped cross-section.

Each support slide 230 comprises a first bracket 230a on which the pair of wheels 232, 233 or 232a, 233a and an opposed wheel 237 are fixed, and a second bracket 230b on which the single wheel 234 or 234a and another opposed wheel 237 are fixed (FIG. 4).

Each support slide 230 comprises a shaft 238 (FIG. 4) coaxial to the axis of rotation R3 and supporting the pick-up member 220. Preferably, bearings are provided between the shaft 238 and the support slide 230, the beatings allowing the pick-up member 220 to rotate with respect to the support slide 230.

During operation of the apparatus 200, the motor drives in rotation the rotor 210 with all the pick-up members 220 associated with it. The rotor 210 reaches at steady operation a constant angular speed set by the operator.

The rotation pins 204b of each pick-up member 220 move at the same angular speed as the rotor 210. The cam followers 204 move by engaging in the eccentric cam 203 of the front body 280. As the cam 203 is eccentric with respect to the axis of rotation R1 of the rotor 210, the rotation pins 204b periodically rotate as a function of the relative position of the cam followers 204 with respect to the eccentric cam 203, causing the levers 205 that displace the support slides 230 with respect to the rotor 210 to oscillate cyclically.

Therefore, during rotation of the rotor 210 at constant speed, the levers 205 accelerate and decelerate the support slides 230 along the rotation direction F2.

It follows that, cyclically, each pick-up member 220 is accelerated in the path between pick-up station 240 and release position 260 and subsequently decelerated in the path between release position 260 and pick-up station 240, passing through the pick-up station 240 with feed pitch P1 and at the release position 260 with deposition pitch P2.

Further, during rotation of the rotor 210, the cam followers 209 move engaging in the spheroconic cam 208 of the rear body 285. The oscillating glyph mechanisms 211 cyclically rotate the respective pick-up members 220 as a function of the relative position of the cam followers 209 with respect to the spheroconic cam 208.

It follows that, cyclically, each pick-up member 220 changes orientation in the path between pick-up station 240 and release position 260 and, subsequently, in the path between release position 260 and pick-up station 240.

Obviously, in order to meet specific and contingent needs, a person skilled in the art can make numerous modifications and variations to the invention described above, all of which being within the scope of protection defined by the following claims.

The invention claimed is:

1. A method for depositing discrete elements on a support element, said discrete elements being separated from each other or joined to each other to form a continuous web having a perforation line between each pair of adjacent discrete elements, comprising:

feeding said discrete elements one after the other into a pick-up station defined at an apparatus comprising a stator and a rotor rotatable about a first axis of rotation along a rotation direction, the rotor comprising a plurality of circumferentially adjacent pick-up elements, wherein the stator comprises a base, a front body and a rear body, the rear body being axially interposed between the rotor and the base, the rotor being axially interposed between the front body and the rear body;

feeding said support element at a release position defined downstream of the pick-up station with reference to said rotation direction;

stably associating each discrete element with a respective pick-up member having in said pick-up station a first orientation with respect to a respective second axis of rotation orthogonal to the first axis of rotation;

moving each pick-up member along said rotation direction from the pick-up station towards the release position with an at least partially accelerated or decelerated motion;

during a movement of each pick-up member along said rotation direction, rotating said pick-up member about the respective second axis of rotation until it takes, at the release position, a second orientation different from said first orientation;

releasing each discrete element from the respective pick-up member on said support element at said release position; and moving each pick-up member along said rotation direction from the release position towards the pick-up station with an at least partially decelerated or accelerated motion;

wherein the movement of each pick-up member about the respective second axis of rotation is obtained by a movement of a second cam follower in a cylindrical or spheroconic cam formed on a radially outer surface of a rear body of the stator, said second cam follower being kinematically coupled to the pick-up member;

wherein the movement of each pick-up member along said rotation direction is obtained by sliding on a pair of annular guides a respective support slide associated with each pick-up member, wherein the rear body is arranged in an axially outer position with respect to the annular guides; and wherein said cylindrical or spheroconic cam is arranged in an axially outer position with respect to said pair of annular guides.

2. The method according to claim 1, wherein the movement of each pick-up member along said rotation direction is obtained by an oscillation of a respective lever with respect to a respective axis parallel to the first axis of rotation, said lever being integral in rotation with the support slide of the pick-up member, said support slide being kinematically connected to a first cam follower coupled to an eccentric cam which is eccentric with respect to the first axis of rotation, said oscillation being obtained by a movement of the first cam follower in the eccentric cam.

3. The method according to claim 1, wherein stably associating each discrete element with the respective pick-up member comprises exerting a suction action on said discrete element through a suction duct associated with said pick-up member and extending at least partially in a radially inner position with respect to said pick-up member.

4. An apparatus for depositing discrete elements on a support element, comprising:

a stator;

a rotor rotatable about a first axis of rotation along a rotation direction and comprising a plurality of circumferentially adjacent pick-up members movable along said rotation direction, each pick-up member being rotatable about a respective second axis of rotation orthogonal to the first axis of rotation, wherein the stator comprises a base, a front body and a rear body, the rear body being axially interposed between the rotor and the base, the rotor being axially interposed between the front body and the rear body;

first control members for controlling a movement of the pick-up members along said rotation direction, said first control members being configured to move the pick-up members between a pick-up station at which the pick-up members have a first relative distance from each other and a release position defined downstream of the pick-up station along said rotation direction and at which the pick-up members have a second relative distance from each other, said second relative distance being different from said first relative distance; and second control members for controlling an orientation of each pick-up member, said second control members being configured to arrange each pick-up member with a first orientation with respect to the respective second axis of rotation when the pick-up members are in the pick-up station and with a second orientation with respect to the respective second axis of rotation when the pick-up members are at said release position, wherein said second control members comprise a cylindrical or spheroconic cam and a plurality of second cam followers coupled to said cylindrical or spheroconic cam, each of said second cam followers being kinematically coupled to a respective pick-up member, wherein said cylindrical or spheroconic cam is formed on a radially outer surface of a rear body of the stator, wherein each pick-up member is associated with a support slide sliding on a pair of annular guides, wherein the rear body is arranged in an axially outer position with respect to the annular guides, and wherein said cylindrical or spheroconic cam is arranged in an axially outer position with respect to said pair of annular guides.

5. The apparatus according to claim 4, wherein said first control members comprise an eccentric cam which is eccentric with respect to the first axis of rotation, a plurality of first cam followers coupled to said eccentric cam and a plurality of levers, each of said levers being integral in rotation with a respective support slide of a pick-up member and being kinematically connected to a respective first cam follower.

6. The apparatus according to claim 5, wherein each of said levers is arranged in an axially inner or axially outer position with respect to said pair of annular guides and it is integrally connected to a portion of the respective support slide which is arranged in an axially inner or axially outer position with respect to said pair of annular guides.

7. The apparatus according to claim 5, wherein said eccentric cam is formed on an axially inner surface of a front body of the stator.

8. The apparatus according to claim 4, wherein each of said second cam followers is kinematically coupled to the respective pick-up member by an oscillating glyph mechanism.

9. The apparatus according to claim 4, wherein a first plurality of support slides comprises a pair of wheels coupled to a radially outer surface of a first annular guide of the pair of annular guides and a single wheel coupled to a radially outer surface of the other annular guide, and a second plurality of support slides comprises a single wheel coupled to the radially outer surface of said first annular guide and a pair of wheels coupled to the radially outer surface of the other annular guide, wherein each support slide of said first plurality of support slides is arranged between two respective support slides of said second plurality of support slides.

10. The apparatus according to claim 4, wherein each pick-up member is in fluid communication with a respective suction conduit that extends at least partially in a radially inner position with respect to said pick-up member.

* * * * *